United States Patent
Reiff et al.

[19]

[11] Patent Number: 5,923,725
[45] Date of Patent: Jul. 13, 1999

[54] MEDICAL X-RAY MACHINE WITH MEANS FOR GENERATING A SOURCE IDENTIFIER ONTO THE X-RAY IMAGE

[75] Inventors: Kurt Reiff, Adelsdorf; Thomas Schmitt, Forchheim, both of Germany

[73] Assignee: Siemens Aktiengesellschaft, Munich, Germany

[21] Appl. No.: 08/931,837

[22] Filed: Sep. 17, 1997

[30] Foreign Application Priority Data

Sep. 17, 1996 [DE] Germany .......................... 196 37 918

[51] Int. Cl.⁶ ............................................. A61B 6/00
[52] U.S. Cl. ................................. 378/162; 378/165
[58] Field of Search ................................. 378/165, 162, 378/163, 166, 207, 204

[56] References Cited

U.S. PATENT DOCUMENTS

| | | | |
|---|---|---|---|
| 2,024,874 | 12/1935 | Prosperi | 378/165 |
| 5,311,567 | 5/1994 | Pellegrino et al. | |
| 5,416,823 | 5/1995 | Livingston | 378/165 X |
| 5,453,813 | 9/1995 | Arnold et al. | |

*Primary Examiner*—David P. Porta
*Attorney, Agent, or Firm*—Sughrue, Mion, Zinn, Macpeak & Seas, PLLC

[57] ABSTRACT

A medical X-ray machine for taking X-ray pictures which includes a radiation source (9), a recording medium (10), and a component, such as a diaphragm (2), for generating at least one machine-specific and/or component-specific marking or data identifier which is automatically assigned to an X-ray picture which is to be or has been taken.

21 Claims, 2 Drawing Sheets

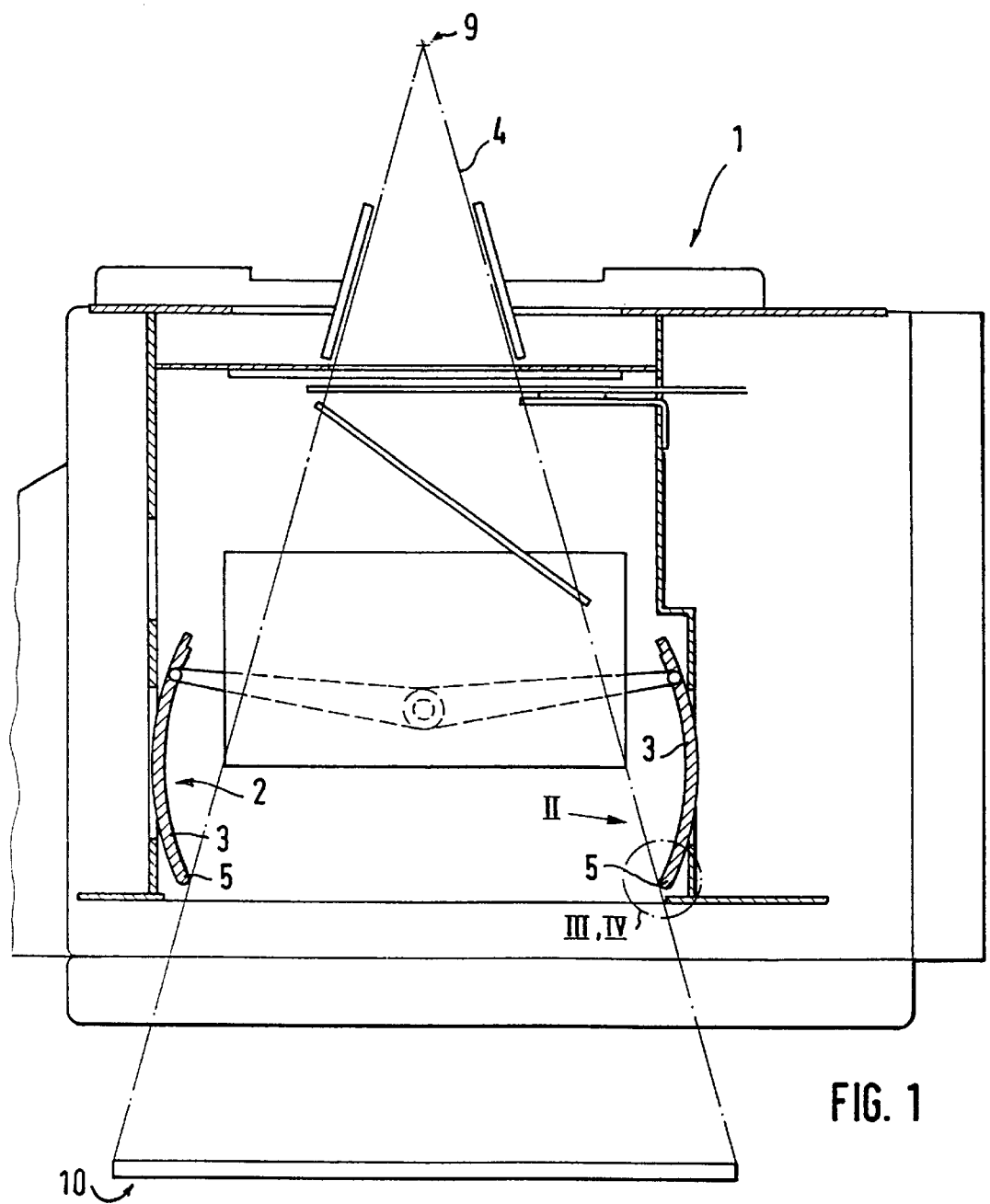
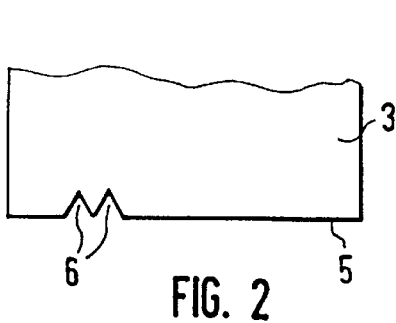
FIG. 2
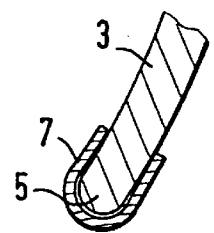
FIG. 3
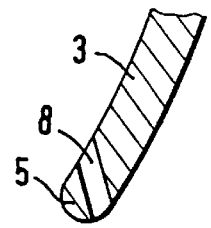
FIG. 4

MEDICAL X-RAY MACHINE WITH MEANS FOR GENERATING A SOURCE IDENTIFIER ONTO THE X-RAY IMAGE

The following disclosure is based on German Patent Application No. 19637918.0, filed on Sep. 17, 1996, which is incorporated into this application by reference.

FIELD AND BACKGROUND OF THE INVENTION

The invention relates to new and useful improvements in medical X-ray machines. More particularly, the invention relates to a medical X-ray machine for taking X-ray pictures, which has a radiation source, a diaphragm device, and a recording medium.

Medical establishments are required by regulation to assign all X-ray pictures taken to the respective recording site, that is to say to the respective X-ray machine used for taking the picture. This is required, e.g., so that each X-ray machine can be tested for constancy by checking and comparing the pictures it has taken. To fulfill this mandate, as a rule the film cassettes are appropriately marked by the radiographer. Alternatively, a suitable marking, for example a combination of letters, is placed on the cassettes and subsequently imaged on the film. Not only is this very cumbersome, since the appropriate identifier has to be separately affixed or applied for each individual picture, but also it is highly prone to errors.

OBJECT OF THE INVENTION

It is therefore an object of the invention to provide an X-ray machine which overcomes the previous disadvantages with regard to correctly assigning a picture to the respective X-ray machine.

SUMMARY OF THE INVENTION

This and other objects are achieved by the teaching of the independent claims. Particularly advantageous refinements of the invention are the subject matter of the dependent claims.

In a medical X-ray machine of the type mentioned above, according to the invention, at least one means is provided for generating at least one machine-specific and/or component-specific marking or data identifier, which is automatically assigned to a picture that is to be or has been taken.

According to the invention, the machine thus contains a means which automatically generates a marking or data identifier which is then automatically assigned to the respective picture. Since the machine assigns the identifier automatically, the need for external marking means or additional manual operations is eliminated. The marking or data identifier is generated or assigned for each individual picture, so there is no possibility of obtaining pictures which, due to a lack of appropriate marking, cannot be assigned after the fact.

Within the scope of a first alternative embodiment, the means are arranged, according to the invention, in the radiation beam path, which extends from the radiation source to the recording medium. This permits an appropriate portion of the means to be imaged on the X-ray picture itself while it is being taken. In this alternative embodiment then, the means is introduced into the beam path and thus automatically imaged on each picture, with the result that it is directly visible thereon. Preferably, the means are expediently provided on the diaphragm device, which bounds the edge of the beam path. Since the diaphragm device bounds the edge of the beam path, arranging the means there ensures that the marking appears only in the edge region of the picture and not in the middle of the image which, as a rule, contains the image of the organ or body part that is to be recorded. It has proven to be particularly expedient in this case if the means is provided on the multileaf diaphragm and/or the iris diaphragm. Within the scope of the invention, the means can be constructed on the edge of the diaphragm as a profile, in particular an indentation, a cutout or the like.

As an addition or alternative thereto, in accordance with the invention, the means can also be constructed as a clip or the like which can be plugged or clipped onto the edge of the diaphragm. These means are therefore advantageously provided on the edge of the respective diaphragm and supply the appropriate marking which is then visible on the picture. It is possible, of course, to provide more than one means in order to increase the number of possible markings or identifiers. The means can also be used in combination with one another.

It is expedient for the clips to consist of metal or a metal alloy. Advantageously, a plurality of clips consisting of different metals or metal alloys are provided. This leads to a different, clip-specific absorption behavior which allows marking in terms of contrast in addition to the simple marking produced by the edge profile of the clips plugged on.

Within the scope of a second alternative according to the invention, the means for generating a data identifier may be an electric means which communicates with a recording medium, including e.g. a digital recording device, and supplies the recording medium with a data identifier to be assigned to the picture data.

In accordance with a design according to this second alternative, it is particularly advantageous to mark the picture with a data identifier generated by an electric means. This data identifier is combined with the picture data obtained from the recording medium as an appropriate marking or coding. The data identifier can be incorporated into the picture data in a variety of ways. For instance, it can be faded into the subsequently displayed picture or otherwise indicated in the latter. Also, the data identifier can be stored together with the picture data in a storage device associated with or incorporated into a digital recording device. Thus, there exist a wide range of different methods for processing the data identifier with the obtained picture data, providing a host of different possibilities for assigning identifiers and thus for documentation.

It has proven to be particularly advantageous to construct the means, in accordance with the invention, as a processor in which a machine-specific and/or component-specific data identifier is stored. The chief advantage of this processor is that it can store a multiplicity of different machine-specific or component-specific identifiers and can thus comprehensively document the entire X-ray machine. This makes it possible not only to specify the particular X-ray machine but also to include in the documentation the different components of the X-ray machine, for example the type of radiation source, the type of diaphragm device, the type of recording medium, and so on.

BRIEF DESCRIPTION OF THE DRAWINGS

The invention, including further advantages, features and refinements of the invention, is explained in more detail below with the aid of diagrammatic, exemplary embodiments in the drawing, in which:

FIG. 1 shows a side view, partially in section, of a diaphragm device integrated in a medical X-ray machine, as a first type of arrangement embodying the invention, FIG. 2 shows a view of a diaphragm plate of the diaphragm device of FIG. 1, in the direction of the arrow II in FIG. 1, FIG. 3 shows an enlarged partial view of the lower edge of a diaphragm plate of FIG. 1, in region III, FIG. 4 shows a further alternative embodiment of the edge region IV of the diaphragm plate of FIG. 1.

DETAILED DESCRIPTION OF THE PREFERRED EMBODIMENTS

Figure 5:
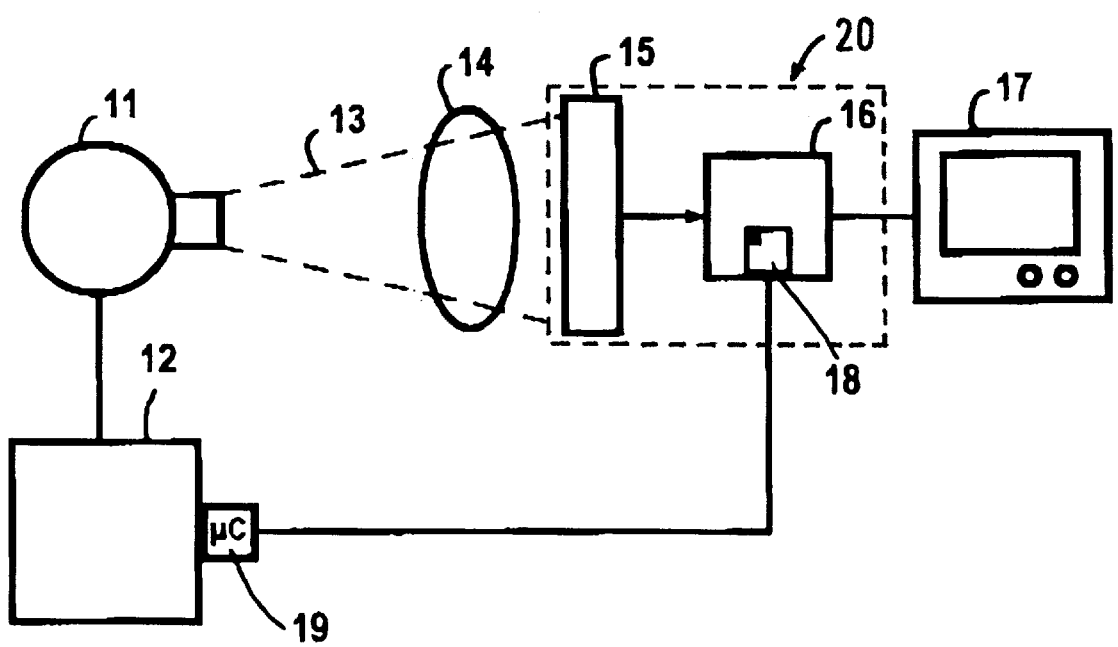
FIG. 5 shows a block-diagram of a medical X-ray machine, as a second type of arrangement embodying the invention.

FIG. 1 shows a diaphragm device 1 arranged between a radiation source 9 and a recording medium 10 of a medical X-ray machine. In addition to a multiplicity of further machine-specific components, the diaphragm device as a multileaf diaphragm 2 including a total of four diaphragm plates 3. Only the two lateral diaphragm plates are represented, in section, in FIG. 1. The diaphragm plates are constructed to be curved essentially in the shape of half shells. They serve to fade the beam path in and out, such that the beam path, which is indicated in outline in FIG. 1 by the dashed and dotted lines 4, is adjusted in the size of its cross-section through operation of the diaphragm plates 3. The radiation is generated by the radiation source 9 and impinges on an area of the recording medium 10 corresponding to the setting selected for the diaphragm plates 3. In other words, the beam path is bounded by the lower plate edges 5 of each of the diaphragm plates 3, as clearly shown in FIG. 1.

As illustrated in FIGS. 2 to 4, the lower diaphragm plate edge 5 of at least one diaphragm plate 3 is provided with an appropriate marking. The marking influences the beam path directly, e.g. by being provided in the beam path, and is consequently visible on the picture obtained. A top view, shown in FIG. 2, of the right-hand diaphragm plate 3 in the direction of the arrow II in FIG. 1 shows that the diaphragm plate edge 5 is provided on one side with two notch-like indentations 6. During operation of the medical X-ray machine, radiation passes through these indentations so that an impression of the notch structure appears at the image border bounding the picture formed with the recording medium 10. The embodiment shown has two indentations by way of example, but different numbers of indentations are possible in order to provide an appropriate identifier for the particular X-ray machine. Other types of edge profiles, for example in the form of waves, incisions, protrusions, or the like, are also feasible.

FIG. 3 shows an enlarged view of an edge-side diaphragm plate section III from FIG. 1 according to another embodiment. In this further embodiment, a clip 7 is fastened onto the diaphragm plate edge 5, thereby gripping the latter and projecting into the beam path. This arrangement also produces a corresponding profile at the border of the picture obtained. The clip 7 may be made from metal or plastic or the like. It is possible here as well to provide a plurality of clips.

FIG. 4 shows a yet another embodiment according to the invention in an enlarged view of the lower diaphragm plate region IV from FIG. 1. The edge 5 of the diaphragm 3 has a cutout 8 through which radiation can pass.

As a result, the radiation exposures performed by that X-ray machine cause an appropriate marking to be imaged onto each picture obtained. Here too the marking may be varied by appropriately changing the type and/or number of cutouts.

One distinct advantage of the above-described embodiments over the conventional art is that the markings need be provided once only, either when the diaphragm plate is manufactured, e.g. if the latter is profiled (FIGS. 2, 4), or else when assembling the X-ray machine, e.g. if plug-on clips are used (FIG. 3). A change is made only if the marking of the machine is to be changed, for example in accordance with a revision of the relevant regulatory stipulations. The marking is automatically assigned to each picture as it is taken, so that additional manual operations on the part of the operator are no longer required.

FIG. 5 illustrates, in block-diagram form, an X-ray diagnostic apparatus having an X-ray tube 11 operated by a high-voltage generator 12. The X-ray tube 11 outputs an X-ray beam 13 that passes through a patient 14 and, attenuated in accordance with the absorption and transparency characteristics of the patient 14, impinges upon an X-ray detector 15.

The X-ray detector 15 converts the X-ray image into electrical signals, which are first processed in a digital imaging system 16 that is coupled to the detector 15, and then, if desired, output to a monitor 17 for the purpose of displaying the X-ray image. The digital imaging system 16 includes, inter alia, conventional components such as processor circuitry, transformers, differential stages, as well as an image memory 18, in which the X-ray image is stored as digital data. The X-ray detector 15, the imaging system 16 and the image memory 18 are all components of an overall, multi-component image recording device 20.

The X-ray detector 15 of an X-ray diagnostic apparatus like the one shown in FIG. 5 preferably includes a photo-diode matrix onto which a scintillation layer has been applied. The scintillation layer transforms the X-ray radiation into light. A video signal representative of the X-ray image is obtained by reading out the charges stored in the photo-diode matrix. The photo-diode matrix can be fashioned, e.g., of amorphous silicium containing hydrogen (aSi:H).

According to the invention, a processor 19 is provided, e.g., on the high-voltage generator 12 and is electrically connected to some portion of the image recording device 20, e.g., the imaging system 16. The processor 19 stores, e.g. in a ROM or an EEPROM, one or more data identifiers that are specific to either the particular X-ray diagnostic apparatus, or to one or more components of the apparatus, or both. As a result, the data identifier constitutes information, in the form of a code or the like, that can be used to identify the X-ray machine and/or components used to produce a given X-ray image. As a result, the data identifier allows individual X-ray images to be uniquely and reliably associated with their source.

Through the electronic link established between the processor 19 and the image recording device 20, the processor supplies the image recording device 20 with the data identifier at some appropriate stage of the X-ray imaging procedure. Preferably, the output of the data identifier from the processor 19 is triggered automatically by some aspect of the radiation procedure, e.g., discharge of a radiation-inducing voltage pulse from the high-voltage generator 12.

In addition, it is preferable that the data identifier is placed into or onto the X-ray picture itself or is otherwise associated with the X-ray image data. For example, if X-ray film is used, the appropriate identifying information can be exposed onto the film sheet of the picture. If the X-ray image is stored in the form of digital data, the identifying data may be stored electronically, e.g. in the same file along with the image data for the particular image recorded in the memory 18. In such a case, the data identifier is preferably displayed alongside or within the display image whenever the image data is displayed on the monitor 17.

The above description of the preferred embodiments has been given by way of example. From the disclosure given, those skilled in the art will not only understand the present invention and its attendant advantages, but will also find apparent various changes and modifications to the structures disclosed. It is sought, therefore, to cover all such changes and modifications as fall within the spirit and scope of the invention, as defined by the appended claims, and equivalents thereof.

What is claimed is:

1. A medical X-ray machine comprising:

a radiation source that outputs radiation for generating radiation image information;

a medium that records the radiation image information; and a component that automatically generates at least one indicium identifying the medical X-ray machine while the radiation image information is generated and automatically assigns the indicium to the radiation image information recorded in the medium.

2. A medical X-ray machine for taking an X-ray picture, the X-ray machine comprising:

a radiation source;

a recording medium; and means for generating at least one indicium identifying the medical X-ray machine and automatically assigning the indicium to the X-ray picture recorded via said recording medium, wherein said radiation source is arranged to emit radiation along a beam path, and wherein said means is arranged in the beam path in such a way that at least a portion of said means is imaged on the X-ray picture taken.

3. The medical X-ray machine as claimed in claim 2, wherein the indicium is predetermined to be specific to the X-ray machine and uniquely identifies the X-ray machine.

4. The medical X-ray machine as claimed in claim 2, wherein the indicium is predetermined to be specific to a preselected component of the X-ray machine.

5. The medical X-ray machine as claimed in claim 2, further comprising a diaphragm device forming an edge boundary of the beam path;

wherein said means is provided on said diaphragm device.

6. The medical X-ray machine as claimed in claim 5, wherein:

said diaphragm device comprises a multi-leaf diaphragm; and said means is provided on said multi-leaf diaphragm.

7. The medical X-ray machine as claimed in claim 5, wherein:

said diaphragm device comprises an iris diaphragm; and said means is provided on said iris diaphragm.

8. The medical X-ray machine as claimed in claim 5, wherein:

said diaphragm device comprises a diaphragm having an edge defining the edge boundary of the beam path; and said means comprises a profile formed on the edge of said diaphragm.

9. The medical X-ray machine as claimed in claim 8, wherein the profile comprises at least one indentation in the edge of said diaphragm.

10. The medical X-ray machine as claimed in claim 8, wherein the profile comprises at least one cutout near the edge of said diaphragm.

11. The medical X-ray machine as claimed in claim 8, wherein the profile comprises at least one projection extending from the edge of said diaphragm radially into the beam path.

12. The medical X-ray machine as claimed in claim 5, wherein:

said diaphragm device comprises a diaphragm having an edge defining the edge boundary of the beam path; and said means comprises an attachment extending from the edge of said diaphragm into the beam path.

13. The medical X-ray machine as claimed in claim 12, wherein said attachment comprises a clip clipped onto the edge of said diaphragm.

14. The medical X-ray machine as claimed in claim 13, wherein said clip is made from metal or a metal alloy.

15. The medical X-ray machine as claimed in claim 13, wherein said attachment comprises a plurality of clips consisting respectively of different metals or metal alloys.

16. A medical X-ray machine for taking an X-ray picture, the X-ray machine comprising:

a radiation source;

a recording medium; and means for generating at least one indicium identifying the medical X-ray machine and automatically assigning the indicium to the X-ray picture recorded via said recording medium, wherein:

said means comprises an electric component configured to communicate with said recording medium and to supply said recording medium with a data identifier as the indicium automatically assigned to the X-ray picture;

said recording medium comprises a digital recording device; and said electric component comprises a processor in which the data identifier is stored as a digital data identifier.

17. A medical X-ray machine for taking an X-ray picture, comprising:

a radiation source and a recording medium, configured to take the X-ray picture; and a component configured to produce, for the X-ray picture, an indicium uniquely identifying the medical X-ray machine used to take the X-ray picture, the indicium being produced automatically while the X-ray picture is taken.

18. The medical X-ray machine as claimed in claim 17, wherein said component is configured to fade a data identifier as the indicium into the X-ray picture.

19. A medical X-ray machine for taking an X-ray picture, the X-ray machine comprising:

a radiation source;

a recording medium; and means for generating at least one indicium identifying the medical X-ray machine and automatically assigning the indicium to the X-ray picture recorded via said recording medium, wherein:
said recording medium comprises a display device configured to display a data identifier, as the indicium, in conjunction with the X-ray picture.

20. A medical X-ray machine for taking an X-ray picture, the X-ray machine comprising:

a radiation source;

a recording medium; and means for generating at least one indicium identifying the medical X-ray machine and automatically assigning the indicium to the X-ray picture recorded via said recording medium, wherein:
said means comprises an electric component configured to communicate with said recording medium and to supply said recording medium with a data identifier as the indicium automatically assigned to the X-ray picture;

said recording medium comprises a digital memory device configured to store image data for the X-ray picture; and said electric component stores the data identifier as a digital data identifier in said digital memory device in conjunction with the image data for the X-ray picture.

21. A medical X-ray machine comprising:

a radiation source configured to emit a beam of radiation;

a recording medium configured to receive the radiation and form a radiation image; and a component configured to influence the beam of radiation so as to produce a predetermined indicium uniquely identifying the medical X-ray machine in at least a portion of the radiation image.

* * * * *